United States Patent
Ono et al.

(10) Patent No.: US 10,288,001 B2
(45) Date of Patent: May 14, 2019

(54) CONTROL SYSTEM OF INTERNAL COMBUSTION ENGINE

(71) Applicant: Toyota Jidosha Kabushiki Kaisha, Toyota-shi Aichi-ken (JP)

(72) Inventors: Yasushi Ono, Susono (JP); Keiichiro Aoki, Sunto-gun Shizuoka-ken (JP); Koji Ide, Gotemba (JP); Go Hayashita, Chigasaki (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 1 day.

(21) Appl. No.: 15/868,578

(22) Filed: Jan. 11, 2018

(65) Prior Publication Data
US 2018/0209364 A1    Jul. 26, 2018

(30) Foreign Application Priority Data
Jan. 26, 2017    (JP) .................................. 2017-012348

(51) Int. Cl.
*F02D 41/04* (2006.01)
*B60W 20/16* (2016.01)
(Continued)

(52) U.S. Cl.
CPC .......... *F02D 41/064* (2013.01); *B60W 10/08* (2013.01); *B60W 20/16* (2016.01);
(Continued)

(58) Field of Classification Search
CPC ............... F02D 41/064; F02D 41/1494; F02D 35/0015; F02D 2250/24; B60W 20/16;
(Continued)

(56) References Cited

U.S. PATENT DOCUMENTS

2005/0205550 A1*   9/2005   Saito ................... F02D 41/1494
                                                                219/497
2009/0116534 A1    5/2009   Tabery et al.
(Continued)

FOREIGN PATENT DOCUMENTS

JP    2007120390 A    5/2007
JP    2008286116 A    11/2008
(Continued)

*Primary Examiner* — Mahmoud Gimie
(74) *Attorney, Agent, or Firm* — Dinsmore & Shohl LLP

(57) ABSTRACT

The control system of an internal combustion engine controls an internal combustion engine comprising an exhaust sensor. The control system comprises a motoring device driving rotation of a crankshaft of the internal combustion engine, a motoring control part configured to control the motoring device, a heater control part configured to control supply of electric power to the heater, and a temperature estimating part configured to estimate a temperature of the sensor element. The motoring control part is configured to drive the motoring device for a predetermined time when the temperature of the sensor element estimated by the temperature estimating part is outside a predetermined cracked element temperature region while the heater control part is supplying electric power to the heater, and stop driving the motoring device when the temperature of the sensor element is within the cracked element temperature region.

10 Claims, 11 Drawing Sheets

(51) Int. Cl.
*F02D 41/06* (2006.01)
*F02D 41/14* (2006.01)
*G01N 27/411* (2006.01)
*F02D 35/00* (2006.01)
*B60W 10/08* (2006.01)
*B60K 6/445* (2007.10)

(52) U.S. Cl.
CPC ..... *F02D 35/0015* (2013.01); *F02D 41/1494* (2013.01); *G01N 27/4118* (2013.01); *B60K 6/445* (2013.01); *B60W 2510/068* (2013.01); *F02D 2250/24* (2013.01)

(58) Field of Classification Search
CPC ............ B60W 10/08; B60W 2510/068; G01N 27/4118; B60K 6/445
USPC .......................................................... 123/697
See application file for complete search history.

(56) References Cited

U.S. PATENT DOCUMENTS

| | | | |
|---|---|---|---|
| 2010/0132680 | A1 | 6/2010 | Iwahashi |
| 2015/0076134 | A1* | 3/2015 | Surnilla .............. F02D 41/1494 219/221 |
| 2016/0139073 | A1* | 5/2016 | Mcquillen .......... G01N 27/4067 205/784.5 |
| 2017/0074147 | A1* | 3/2017 | Sakashita .............. F01N 11/002 |
| 2017/0261463 | A1* | 9/2017 | Sugiura .............. G01N 27/4071 |
| 2018/0128149 | A1* | 5/2018 | McQuillen ............ F02D 41/005 |

FOREIGN PATENT DOCUMENTS

| | | |
|---|---|---|
| JP | 2009-529691 A | 8/2009 |
| JP | 2009299538 A | 12/2009 |

* cited by examiner

CONTROL SYSTEM OF INTERNAL COMBUSTION ENGINE

CROSS-REFERENCE TO RELATED APPLICATIONS

This application claims priority to Japanese Patent Application No. 2017-012348 filed on Jan. 26, 2017, the entire contents of which are hereby incorporated by reference.

TECHNICAL FIELD

The present disclosure relates to a control system of an internal combustion engine.

BACKGROUND ART

It has been known in the past to place an exhaust sensor in an exhaust passage of an internal combustion engine to detect a specific component in exhaust gas (for example, see Japanese Patent Publication No. 2009-299538A). Such an exhaust sensor is provided with a sensor element, a sensor cover covering the sensor element, and a heater heating the sensor element. The exhaust sensor is arranged in an exhaust pipe so as to be exposed to the exhaust gas. Part of the exhaust gas flows into the sensor element.

When the temperature of the exhaust pipe is the dew point of water or less, the water vapor in the exhaust gas condenses and condensed water is produced. Part of the condensed water enters into the sensor cover of the exhaust sensor. When there is condensed water inside the sensor cover, if exhaust gas flows into the sensor cover, drops of the condensed water will strike the sensor element together with the exhaust gas. If the sensor element does not have water repellency, the drops of water striking the sensor element will penetrate into the sensor element. Further, if the temperature of the sensor element is high due to heating by the heater, the water drops penetrating into the sensor element will evaporate inside the sensor element. As a result, the sensor element will be given thermal shock and the sensor element will sometimes crack.

Regarding this problem, Japanese Patent Publication No. 2009-299538A describes to prevent a cracked element of the exhaust sensor by raising the temperature of the exhaust system by driving a crankshaft to rotate by a motoring means before starting up the internal combustion engine and making the heater start after the ambient temperature of the exhaust sensor reaches the dew point.

SUMMARY

Technical Problem

However, if delaying the start of the heater until the ambient temperature of the exhaust sensor reaches the dew point, the time until the sensor element becomes activated becomes longer. As a result, it is not possible to perform control of the air-fuel ratio based on the output of the exhaust sensor earlier and the exhaust emission is liable to deteriorate.

Therefore, an object of some embodiments of the present disclosure is to prevent water coverage from causing a cracked element of an exhaust sensor in an internal combustion engine provided with the exhaust sensor while realizing earlier activation of the sensor element.

Solution to Problem

The summary of the present disclosure is as follows.

A first aspect includes a control system of an internal combustion engine controlling an internal combustion engine comprising an exhaust sensor arranged in an exhaust passage and detecting a specific component in exhaust gas. The exhaust sensor comprises a sensor element, a sensor cover covering the sensor element, and a heater heating the sensor element. The control system comprises a motoring device driving rotation of a crankshaft of the internal combustion engine, a motoring control part configured to control the motoring device, a heater control part configured to control supply of electric power to the heater, and a temperature estimating part configured to estimate a temperature of the sensor element. The motoring control part is configured to drive the motoring device for a predetermined time when the temperature of the sensor element estimated by the temperature estimating part is outside a predetermined cracked element temperature region while the heater control part is supplying electric power to the heater, and stop driving the motoring device when the temperature of the sensor element is within the cracked element temperature region.

A second aspect includes the control system of an internal combustion of the first aspect and further includes a water amount estimating part estimating an amount of water present inside the sensor cover, wherein the motoring control part is configured to control the motoring device based on the amount of water estimated by the water amount estimating part.

A third aspect includes the control system of an internal combustion engine of the second aspect, wherein the motoring control part is configured to stop driving the motoring device when the amount of water estimated by the water amount estimating part is a predetermined reference value or less even when the temperature of the sensor element estimated by the temperature estimating part is outside the cracked element temperature region.

A fourth aspect includes the control system of an internal combustion engine of either the second aspect or the third aspect, wherein the motoring control part is configured to lengthen the predetermined time when the amount of water estimated by the water amount estimating part is relatively large compared to when the amount of water is relatively small.

A fifth aspect includes the control system of an internal combustion engine of any one of the first through fourth aspects, wherein the temperature estimating part is configured to estimate the temperature of the sensor element based on the total of the electric power supplied to the heater.

Advantageous Effects

According to the present disclosure, it is possible to prevent water coverage from causing a cracked element of an exhaust sensor in an internal combustion engine provided with the exhaust sensor while realizing earlier activation of the sensor element.

DETAILED DESCRIPTION

Figure 1:
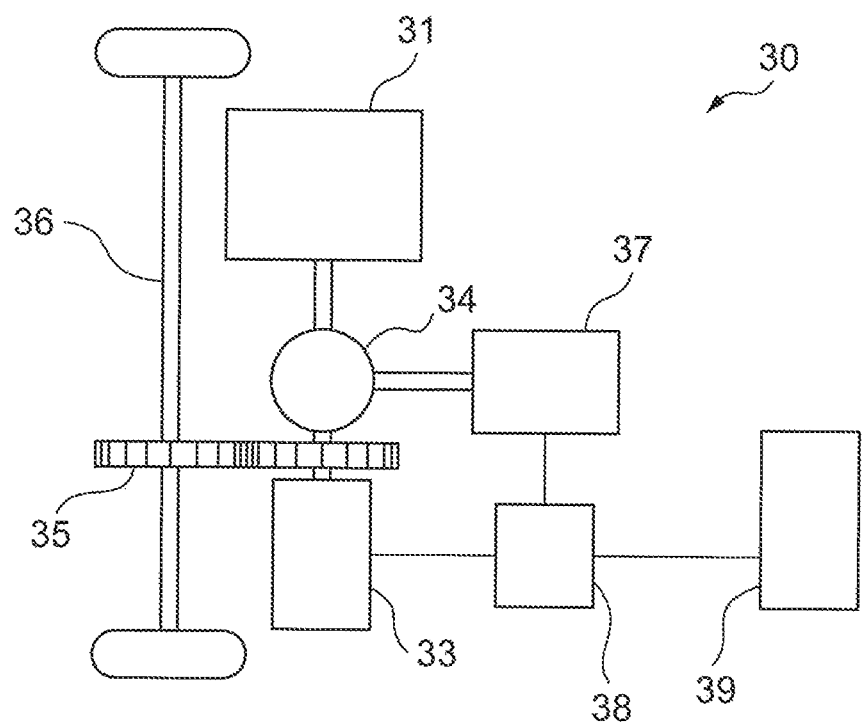
FIG. 1 schematically shows a vehicle to which a control system of an internal combustion engine according to a first embodiment of the present disclosure is applied.

Below, referring to the drawings, embodiments of the present disclosure will be explained in detail. Note that, in the following description, similar component elements will be assigned the same reference numerals.

First Embodiment

First, referring to FIG. 1 to FIG. 7, a first embodiment of the present disclosure will be explained.

<Explanation of Vehicle as a Whole>

FIG. 1 schematically shows a vehicle 30 to which a control system of an internal combustion engine of the first embodiment of the present disclosure is applied. The vehicle 30 is provided with an internal combustion engine 31 and a motor 33 as sources of drive power of a wheel shaft 36. The vehicle 30 is a so-called "hybrid" vehicle.

The internal combustion engine 31 is coupled through a drive power division mechanism 34 and a speed reducer 35 with a wheel shaft 36. The motor 33 is coupled through the speed reducer 35 with the wheel shaft 36. Therefore, the wheel shaft 36 is driven by the output of one or both of the internal combustion engine 31 and motor 33. Further, the drive power division mechanism 34 is coupled with a generator 37. The output of the internal combustion engine 31 is transmitted through the drive power division mechanism 34 to one or both of the wheel shaft 36 and generator 37.

The motor 33 and generator 37 are electrically connected through a power control unit 38 including an inverter and converter to a battery 39. Electric power generated at the generator 37 due to the drive force of the internal combustion engine 31 is supplied through the power control unit 38 to the motor 33 or battery 39. The electric power supplied to the battery 39 is stored in the battery 39.

Further, at the time of deceleration of the vehicle 30, the motor 33 can be made to generate electric power by the drive power of the wheel shaft 36. The electric power generated by the motor 33 is supplied through the power control unit 38 to the battery 39. The electric power supplied to the battery 39 is stored in the battery 39. Therefore, in the vehicle 30, the kinetic energy of the vehicle 30 can be recovered at the battery 39.

Figure 2:
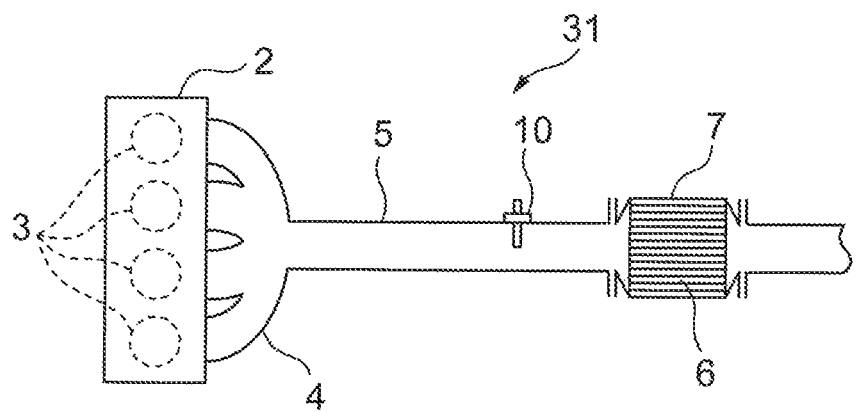
FIG. 2 schematically shows an engine body and exhaust passage of an internal combustion engine.

FIG. 2 is a view schematically showing an engine body 2 and exhaust passage of an internal combustion engine 31. In FIG. 2, illustration of the intake passages for introducing air into the combustion chambers of the cylinders 3 is omitted. The engine body 2 of the internal combustion engine 31 is coupled with an exhaust manifold 4. The exhaust manifold 4 is coupled through an exhaust pipe 5 to a casing 7 housing an exhaust purification catalyst 6. The exhaust purification catalyst 6 is, for example, a ternary catalyst removing the HC, CO, $NO_x$, etc., in the exhaust gas. The exhaust manifold 4 and exhaust pipe 5 form an exhaust passage for discharging exhaust gas generated by combustion of the air-fuel mixture in the combustion chambers from the cylinders 3.

<Explanation of Air-Fuel Ratio Sensor>

In the present embodiment, the internal combustion engine 31 is provided with an air-fuel ratio sensor 10 as an exhaust sensor detecting a specific component in the exhaust gas. The air-fuel ratio sensor 10 is arranged in the exhaust passage of the internal combustion engine 31. Specifically, the air-fuel ratio sensor 10 is arranged in the exhaust pipe 5 at the upstream side of the exhaust purification catalyst 6 in the direction of flow of exhaust gas. The air-fuel ratio sensor 10 detects the concentration of oxygen in the exhaust gas to thereby linearly detect the air-fuel ratio of the exhaust gas. Note that, the air-fuel ratio sensor 10 may be arranged at another position in the exhaust passage. For example, the air-fuel ratio sensor 10 may be arranged in the exhaust pipe at the downstream side of the exhaust purification catalyst 6 in the direction of flow of exhaust gas.

Figure 3:
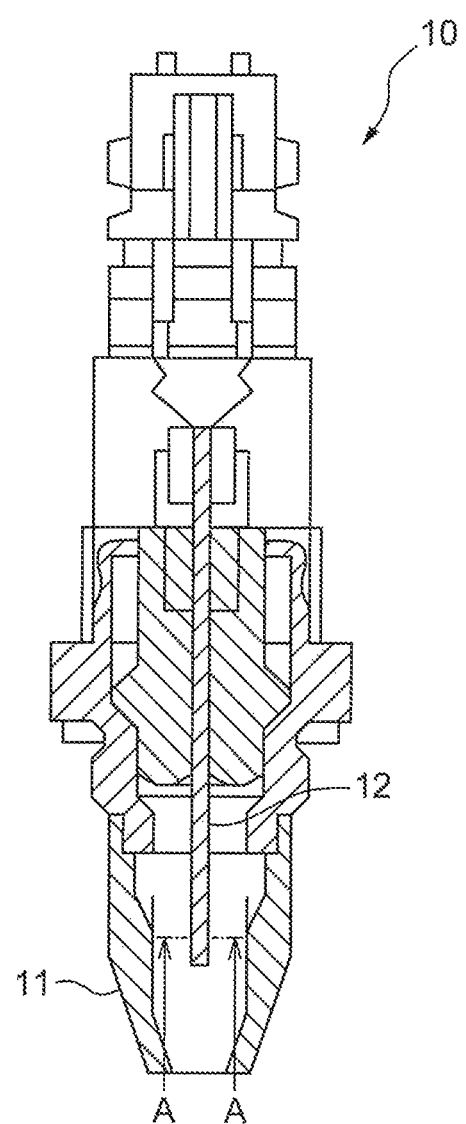
FIG. 3 is an enlarged view of an air-fuel ratio sensor.

Below, referring to FIG. 3 and FIG. 4, the configuration of the air-fuel ratio sensor 10 will be explained. FIG. 3 is an enlarged view of the air-fuel ratio sensor 10. In FIG. 3, the front end side of the air-fuel ratio sensor 10 is shown by a cross-sectional view. The air-fuel ratio sensor 10 is fastened to the exhaust pipe 5 in the state with the front end side (the lower side in FIG. 3) inserted inside the exhaust pipe 5. The air-fuel ratio sensor 10 is provided with a sensor element 12, and a sensor cover 11 covering the sensor element 12. The sensor element 12 is arranged in the sensor cover 11 and has a plate-like shape.

Figure 4:
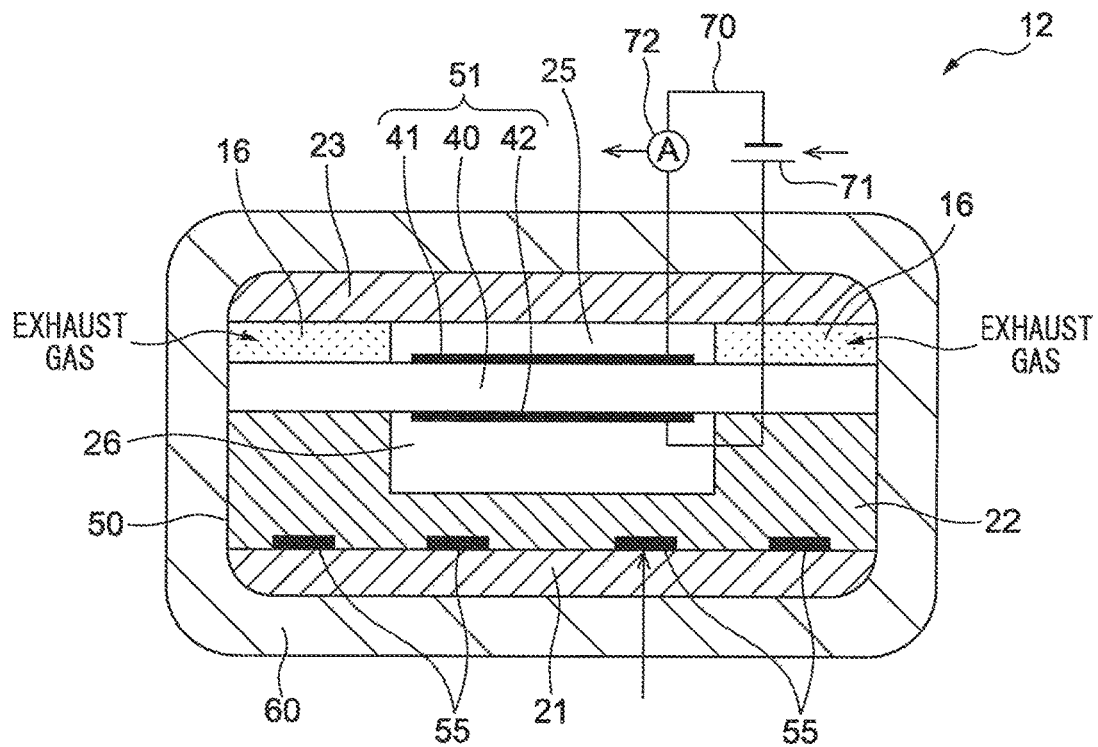
FIG. 4 is a cross-sectional view of a sensor element of an air-fuel ratio sensor along the line A-A of FIG. 3.

FIG. 4 is a cross-sectional view of a sensor element 12 of the air-fuel ratio sensor 10 along the line A-A of FIG. 3. As shown in FIG. 4, the sensor element 12 is provided with an element body 50 provided with a sensor cell 51 and a protective layer 60 formed on the outer surface of the element body 50.

The element body 50 is formed with a measured gas chamber 25 and a reference gas chamber 26. When the air-fuel ratio sensor 10 is arranged in the exhaust passage of the internal combustion engine 31, exhaust gas flowing through the exhaust passage is introduced into the measured gas chamber 25 as the measured gas. Reference gas is introduced into the reference gas chamber 26. The reference gas is for example the atmosphere. In this case, the reference gas chamber 26 is opened to the atmosphere.

The air-fuel ratio sensor 10 is a laminate type air-fuel ratio sensor comprised of a plurality of layers laminated together. The element body 50 is provided with a solid electrolyte layer 40, diffusion regulating layer 16, first barrier layer 21, second barrier layer 22, and third barrier layer 23. The solid electrolyte layer 40 is a thin plate member having oxide ion conductivity. The solid electrolyte layer 40 is, for example, a sintered body of $ZrO_2$ (zirconia), $HfO_2$, $ThO_2$, $Bi_2O_3$, etc. to which CaO, MgO, $Y_2O_3$, $Yb_2O_3$, etc. is added as a stabilizer. The diffusion regulating layer 16 is a thin plate member having gas permeability. The diffusion regulating layer 16 is, for example, comprised of alumina, magnesia, silica, spinel, mullite, or other porous ceramic. The barrier layers 21 to 23 are gas barrier type thin sheet members, and, for example, include alumina.

The layers of the element body 50 are comprised of, from the bottom of FIG. 4, the first barrier layer 21, second barrier layer 22, solid electrolyte layer 40, diffusion regulating layer 16, and third barrier layer 23 stacked in that order. The measured gas chamber 25 is formed and defined by the solid electrolyte layer 40, diffusion regulating layer 16, and third barrier layer 23. The exhaust gas passes through the protective layer 60 and diffusion regulating layer 16 and is introduced to the inside of the measured gas chamber 25. The diffusion regulating layer 16 regulates the diffusion of the measured gas. Note that, the measured gas chamber 25 may be configured in any form so long as adjoining the solid electrolyte layer 40 and having the measured gas introduced into it.

The reference gas chamber 26 is formed and defined by the solid electrolyte layer 40 and the second barrier layer 22. Note that, the reference gas chamber 26 may be configured in any form so long as adjoining the solid electrolyte layer 40 and having the reference gas flow into it.

The sensor cell 51 is an electrochemical cell having a solid electrolyte layer 40, first electrode 41, and second electrode 42. The first electrode 41 is arranged on the surface of the solid electrolyte layer 40 on the measured gas chamber 25 side so that it is exposed to the measured gas of the measured gas chamber 25. On the other hand, the second electrode 42 is arranged on the surface of the solid electrolyte layer 40 on the reference gas chamber 26 side so that it is exposed to the reference gas inside the reference gas chamber 26. The first electrode 41 and the second electrode 42 are arranged so as to face each other across the solid electrolyte layer 40. The first electrode 41 and second electrode 42 are comprised of platinum (Pt) or another precious metal with a high catalytic activity. For example, the first electrode 41 and second electrode 42 are porous cermet electrodes including mainly Pt.

The protective layer 60 is formed on the outer surface of the element body 50 so as to cover the entire outer surface of the element body 50. The protective layer 60 has a gas permeability and is comprised of alumina, titania, zirconia, silicon carbide, silicon nitride, zinc oxide, and other porous ceramic.

The protective layer 60 has water repellency when its temperature is high. This property is obtained by generating the Leidenfrost phenomenon. The "Leidenfrost phenomenon" is the phenomenon where when drops of water strike a high temperature protective layer 60, a film of water vapor is formed between the protective layer 60 and drops of water whereby transfer of heat between the protective layer 60 and the drops of water is suppressed. If the Leidenfrost phenomenon occurs, the drops of water are repelled from the protective layer 60, so water is kept from penetrating the protective layer 60.

The air-fuel ratio sensor 10 is further provided with a heater 55. The heater 55 is arranged in the sensor element 12 and heats the sensor element 12. Specifically, the heater 55 is arranged between the first barrier layer 21 and the second barrier layer 22. The heater 55 is, for example, a thin plate member of cermet including platinum (Pt) and ceramic (for example, alumina etc.) and forms a heat generating element generating heat by conduction of current.

The first electrode 41 and second electrode 42 of the sensor cell 51 are connected to an electrical circuit 70. The electrical circuit 70 is provided with a power supply 71 and current detector 72. The power supply 71 applies voltage across the electrodes so that the potential of the second electrode 42 becomes higher than the potential of the first electrode 41. Further, the current detector 72 detects the current flowing through the sensor cell 51 as the output of the sensor cell 51. The air-fuel ratio sensor 10 detects the limit current flowing through the sensor cell 51 when applying predetermined voltage to the sensor cell 51 so as to detect the air-fuel ratio of the exhaust gas. Therefore, the air-fuel ratio sensor 10 in the present embodiment is a so-called limit current type air-fuel ratio sensor.

In this regard, when the temperature of the exhaust pipe 5 is the dew point of water or below, the water vapor in the exhaust gas condenses and condensed water is formed. Part of this condensed water enters the inside of the sensor cover 11 of the air-fuel ratio sensor 10. When there is condensed water inside the sensor cover 11, if exhaust gas flows into the sensor cover 11, drops of condensed water will strike the sensor element 12 together with the exhaust gas. If the temperature of the sensor element 12 is high due to heating by the heater 55, the drops of water penetrating inside the sensor element 12 will evaporate inside the sensor element 12. As a result, sometimes the sensor element 12 will be given thermal shock and the sensor element 12 will crack.

However, when the above-mentioned Leidenfrost phenomenon occurs, drops of water are repelled by the protective layer 60. For this reason, water is kept from penetrating inside the sensor element 12 and a cracked element of the air-fuel ratio sensor 10 (cracking of the sensor element 12) can be prevented. Further, when the temperature of the sensor element 12 is low, drops of water do not evaporate in the sensor element 12, so no cracked element of the air-fuel ratio sensor 10 is caused.

Further, if condensed water is present inside the sensor cover 11, the rise of temperature of the sensor element 12 at the time of heating by the heater 55 becomes slower and the time taken for the sensor element 12 to be activated becomes longer. As a result, it is not possible to quickly control the air-fuel ratio based on the output of the air-fuel ratio sensor 10 and the exhaust emission is liable to deteriorate.

<Explanation of Control System of Internal Combustion Engine>

Figure 5:
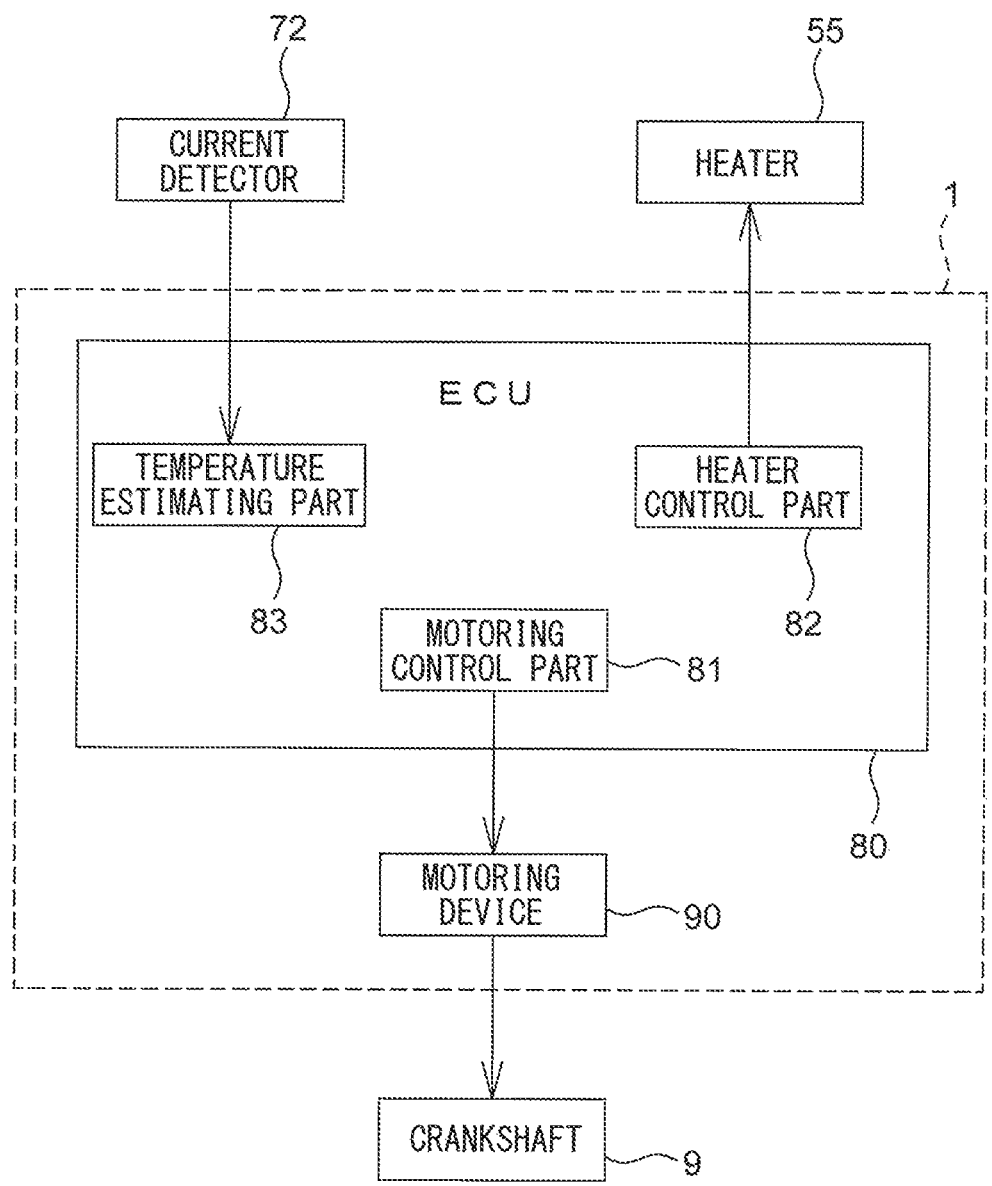
FIG. 5 is a block diagram schematically showing the configuration of a control system of an internal combustion engine etc., according to a first embodiment of the present disclosure.

To solve the above problem, the control system of an internal combustion engine according to the first embodiment of the present disclosure performs the following control: FIG. 5 is a block diagram schematically showing the configuration of a control system of an internal combustion engine 1 etc., according to the first embodiment of the present disclosure. The control system of an internal combustion engine 1 is provided with a motoring device 90 and electronic control unit (ECU) 80. The motoring device 90 drives rotation of the crankshaft 9 of the internal combustion engine 31. In the present embodiment, the generator 37 shown in FIG. 1 is used as the motoring device 90.

The ECU 80 is a microcomputer provided with components connected to each other by bidirectional buses such as a central processing unit (CPU), read only memory (ROM), random access memory (RAM), input port, and output port. The ECU 80 includes a motoring control part 81, heater control part 82, and temperature estimating part 83. Therefore, the control system of an internal combustion engine 1 is provided with the motoring control part 81, heater control part 82, and temperature estimating part 83. The motoring control part 81 controls the motoring device 90. The heater control part 82 controls the supply of electric power to the heater 55. The temperature estimating part 83 estimates the temperature of the sensor element 12 of the air-fuel ratio sensor 10.

The temperature estimating part 83, for example, calculates the temperature of the sensor element 12 based on the impedance of the sensor cell 51. The temperature estimating part 83 calculates the impedance of the sensor cell 51 based on the output of the sensor cell 51 detected by the current detector 72 when a high frequency voltage is supplied from the power supply 71 to the sensor cell 51. Note that, the temperature estimating part 83 may calculate the temperature of the sensor cell 51 based on the resistance across electrodes of the sensor cell 51.

Further, the temperature estimating part 83 may estimate the temperature of the sensor element 12 based on the total of the electric power W supplied to the heater 55. Due to this, even if the impedance or resistance across electrodes of the sensor cell 51 cannot be detected, the temperature of the sensor element 12 can be estimated. Further, it is possible to prevent the temperature of the sensor element 12 from being estimated lower than the actual temperature when the sensor cell 51 rises in impedance due to degradation of the sensor element 12, etc.

The electric power W is approximated by the next formula. The total of the electric power W is calculated by cumulatively adding the electric power W during the operating time of the heater 55.

$$W \approx Duty \times V \times V$$

In the above formula, "Duty" is the duty ratio (%) when the heater control part 82 supplies electric power to the heater 55 by PWM control. Further, "V" is the voltage (V) of the battery 39.

The estimated temperature of the sensor element 12 is calculated by multiplying a predetermined conversion coefficient with the total of the electric power W. Further, the estimated temperature of the sensor element 12 may be calculated using a map showing the relationship between the total of the electric power W and the estimated temperature of the sensor element 12. In this map, the estimated temperature of the sensor element 12 is made higher the larger the total of the electric power W.

If the motoring device 90 drives rotation of the crankshaft 9, the air discharged from the insides of the cylinders 3 flows into the sensor cover 11. The air causes the water inside the sensor cover 11 to be drained to outside of the sensor cover 11. However, at this time, drops of water are liable to strike the sensor element 12. For this reason, the motoring control part 81 drives the motoring device 90 for a predetermined time when the temperature of the sensor element 12 estimated by the temperature estimating part 83 is outside the cracked element temperature region while the heater control part 82 is supplying electric power to the heater 55, and stops driving the motoring device 90 when the temperature of the sensor element 12 is within the cracked element temperature region. The cracked element temperature region is a temperature region where the sensor element 12 would crack due to drops of water striking it and is determined in advance by experiments or calculation. The cracked element temperature region is, for example, a temperature between the boiling point of water and the lowest temperature at which the Leidenfrost phenomenon will occur at the outer surface of the sensor element 12 (protective layer 60).

In the above-mentioned control, the motoring device 90 is driven only when the temperature of the sensor element 12 is outside the cracked element temperature region, so it is possible to prevent water coverage from causing a cracked element of the air-fuel ratio sensor 10 while promoting discharge of water from the sensor cover 11. Further, regardless of the ambient temperature of the air-fuel ratio sensor 10, it is possible to supply electric power to the heater 55 to heat the air-fuel ratio sensor 10. For this reason, due to the above-mentioned control, it is possible to prevent water coverage from causing a cracked element of the air-fuel ratio sensor 10 while realizing earlier activation of the sensor element 12.

<Explanation of Control using Time Chart>

Figure 6:
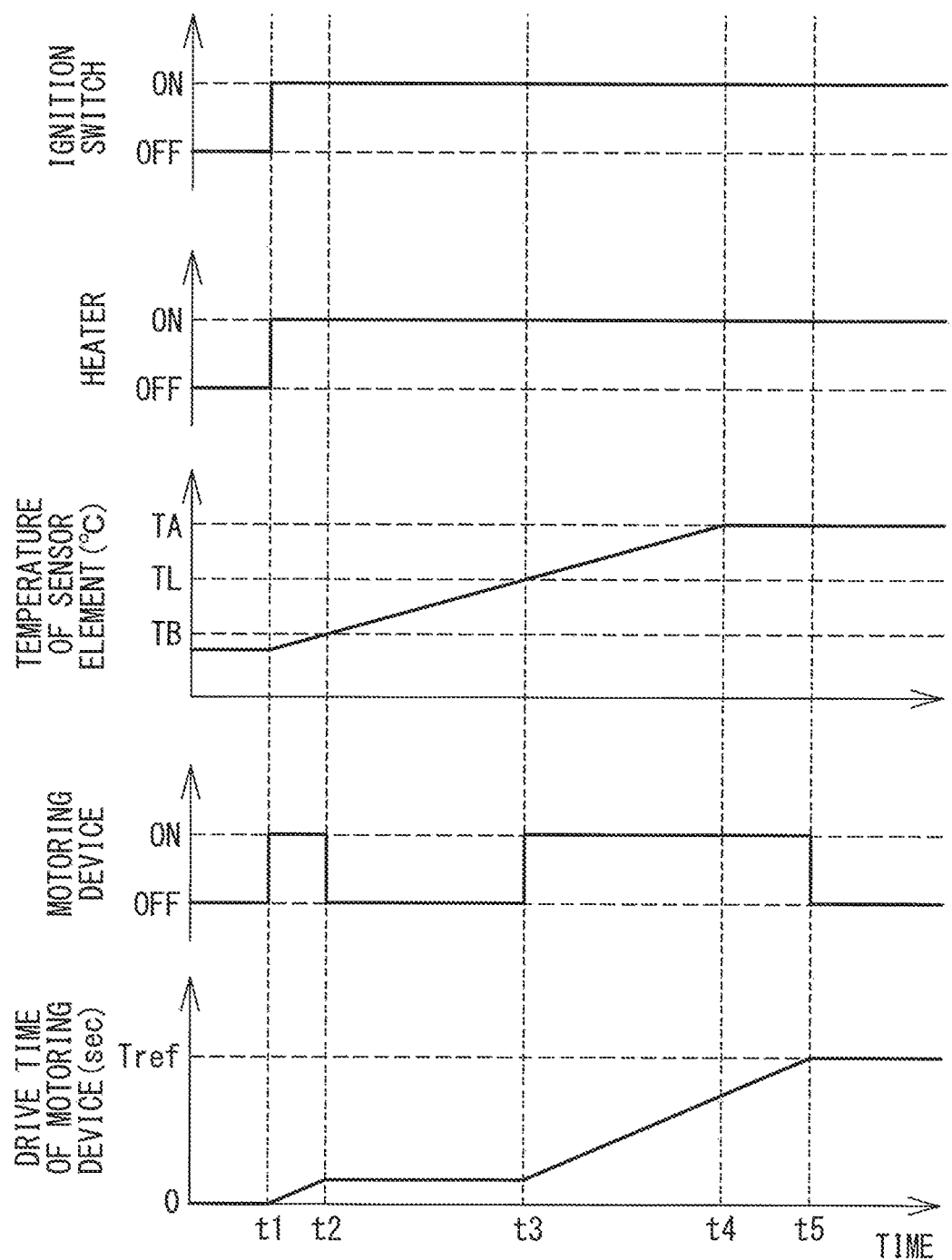
FIG. 6 is a time chart of on/off operation of an ignition switch etc., of the vehicle.

Below, referring to the time chart of FIG. 6, the control performed by the control system of an internal combustion engine 1 will be specifically explained. FIG. 6 is a time chart of the on/off operation of the ignition switch of the vehicle 30, on/off operation of the heater 55, temperature of the sensor element 12, on/off state of the motoring device 90, and drive time of the motoring device 90.

In the illustrated example, at the time t1, the ignition switch of the vehicle 30 is turned on. If the ignition switch is turned on, the supply of electric power to the heater 55 is started. Further, at the time t1, the temperature of the sensor element 12 is lower than the boiling point TB of water (100° C.). For this reason, at the time t1, the motoring device 90 is started.

After the time t1, at the time t2, the temperature of the sensor element 12 reaches the boiling point TB of water. For this reason, at the time t2, the drive operation of the motoring device 90 is stopped. After that, at the time t3, the temperature of the sensor element 12 reaches the lowest temperature TL at which the Leidenfrost phenomenon occurs at the outer surface of the sensor element 12 (in this example, 400° C.). For this reason, at the time t3, the motoring device 90 is again started up.

After that, at the time t4, the temperature of the sensor element 12 reaches the activation temperature TA of the sensor element 12 (in this example, 700° C.). To maintain the temperature of the sensor element 12 at the activation temperature TA, electric power continues to be supplied to the heater 55 even after the time t4. After that, at the time t5, the total drive time of the motoring device 90 reaches the predetermined time Tref (in this example, 5 seconds) and the drive operation of the motoring device 90 is stopped.

Note that, when the temperature of the sensor element 12 is within the cracked element temperature region (time t2 to time t3), to prevent the exhaust gas from causing drops of water in the sensor cover 11 to strike the sensor element 12, the air-fuel mixture stops being burned in the cylinders 3 of the internal combustion engine 31. For example, the internal combustion engine 31 is started when the total drive time of the motoring device 90 reaches the predetermined time Tref and the drive operation of the motoring device 90 is stopped (time t5). In the present embodiment, even before the internal combustion engine 31 is started, the motor 33 can drive the vehicle 30.

<Control Routine of Processing for Draining Water>

Figure 7:
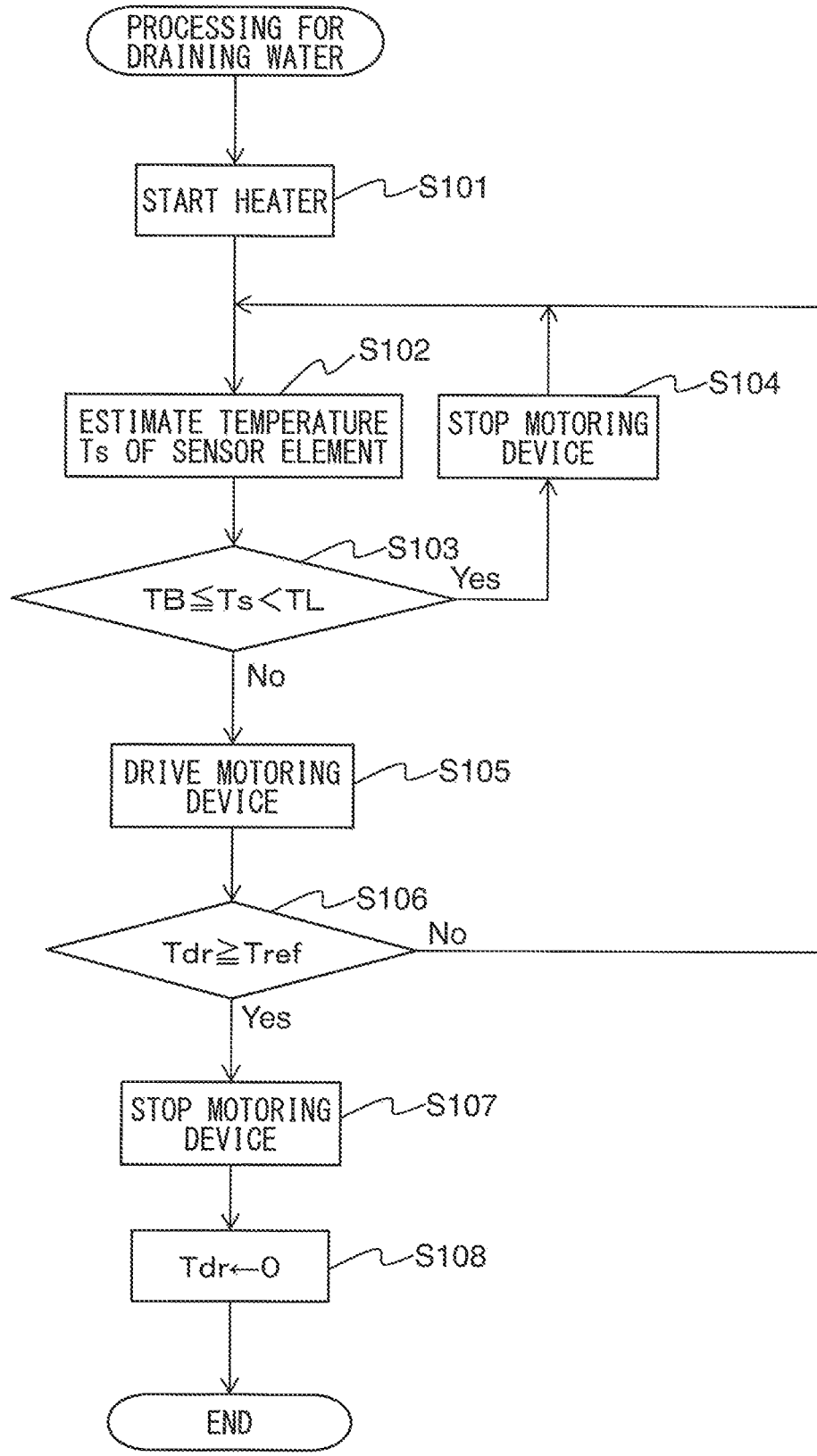
FIG. 7 is a flow chart showing a control routine of processing for draining water in the first embodiment of the present disclosure.

FIG. 7 is a flow chart showing a control routine of processing for draining water in the first embodiment of the present disclosure. The present control routine is executed by the ECU 80 when the ignition switch of the vehicle 30 is turned on. In the present control routine, the drive operation of the motoring device 90 is controlled so as to prevent a cracked element of the air-fuel ratio sensor 10 while draining water in the sensor cover 11.

First, at step S101, the heater control part 82 starts up the heater 55. In other words, the heater control part 82 starts the supply of electric power to the heater 55. Next, at step S102, the temperature estimating part 83 estimates the temperature Ts of the sensor element 12 by any of the above methods.

Next, at step S103, the motoring control part 81 judges whether the temperature Ts of the sensor element 12 is within the cracked element temperature region. For example, the motoring control part 81 judges whether the temperature Ts of the sensor element 12 is the boiling point TB of water or more and lower than the lowest temperature TL at which the Leidenfrost phenomenon occurs at the outer surface of the sensor element 12. The boiling point TB of water is 100° C. at atmospheric pressure (1 atm). Further, the lowest temperature TL at which the Leidenfrost phenomenon occurs at the outer surface of the sensor element 12 is the lower limit value of temperature at which the Leidenfrost phenomenon will occur when an extremely small amount of water drops strike the sensor element 12, and, for example, is 400° C.

If at step S103 it is judged that the temperature Ts of the sensor element 12 is within the cracked element temperature region, the present control routine proceeds to step S104. At step S104, in order to prevent a cracked element of the air-fuel ratio sensor 10, the motoring control part 81 stops the operation for driving the motoring device 90. After step S104, the present control routine returns to step S102.

On the other hand, if at step S103 it is judged that the temperature Ts of the sensor element 12 is outside the cracked element temperature region, the present control routine proceeds to step S105. At step S105, the motoring control part 81 drives the motoring device 90. As a result, the crankshaft 9 is driven to rotate by the motoring device 90, and the water inside the sensor cover 11 is drained by the air discharged from inside the cylinders 3.

Next, at step S106, the motoring control part 81 judges whether the total drive time Tdr of the motoring device 90 is a predetermined time Tref or more. The predetermined time Tref is the time required for draining a predetermined amount of water inside the sensor cover 11 and is set in advance through experiments or calculation.

If at step S106 it is judged that the total drive time Tdr is less than the predetermined time Tref, the present control routine returns to step S102. On the other hand, if at step S106 it is judged that the total drive time Tdr is the predetermined time Tref or more, the present control routine proceeds to step S107. At step S107, the motoring control part 81 stops driving the motoring device 90. Therefore, until the total drive time Tdr reaches the predetermined time Tref, the motoring device 90 is continuously or intermittently driven. Note that, the initial value of the total drive time Tdr is zero.

After step S107, at step S108, the motoring control part 81 resets the total drive time Tdr to zero. After step S108, the present control routine is ended.

Second Embodiment

The configuration and control of the control system of an internal combustion engine according to a second embodiment are basically similar to the configuration and control of the control system of an internal combustion engine according to the first embodiment except for the points explained below. For this reason, below, the second embodiment of the present disclosure will be explained focusing on the parts different from the first embodiment.

Figure 8:
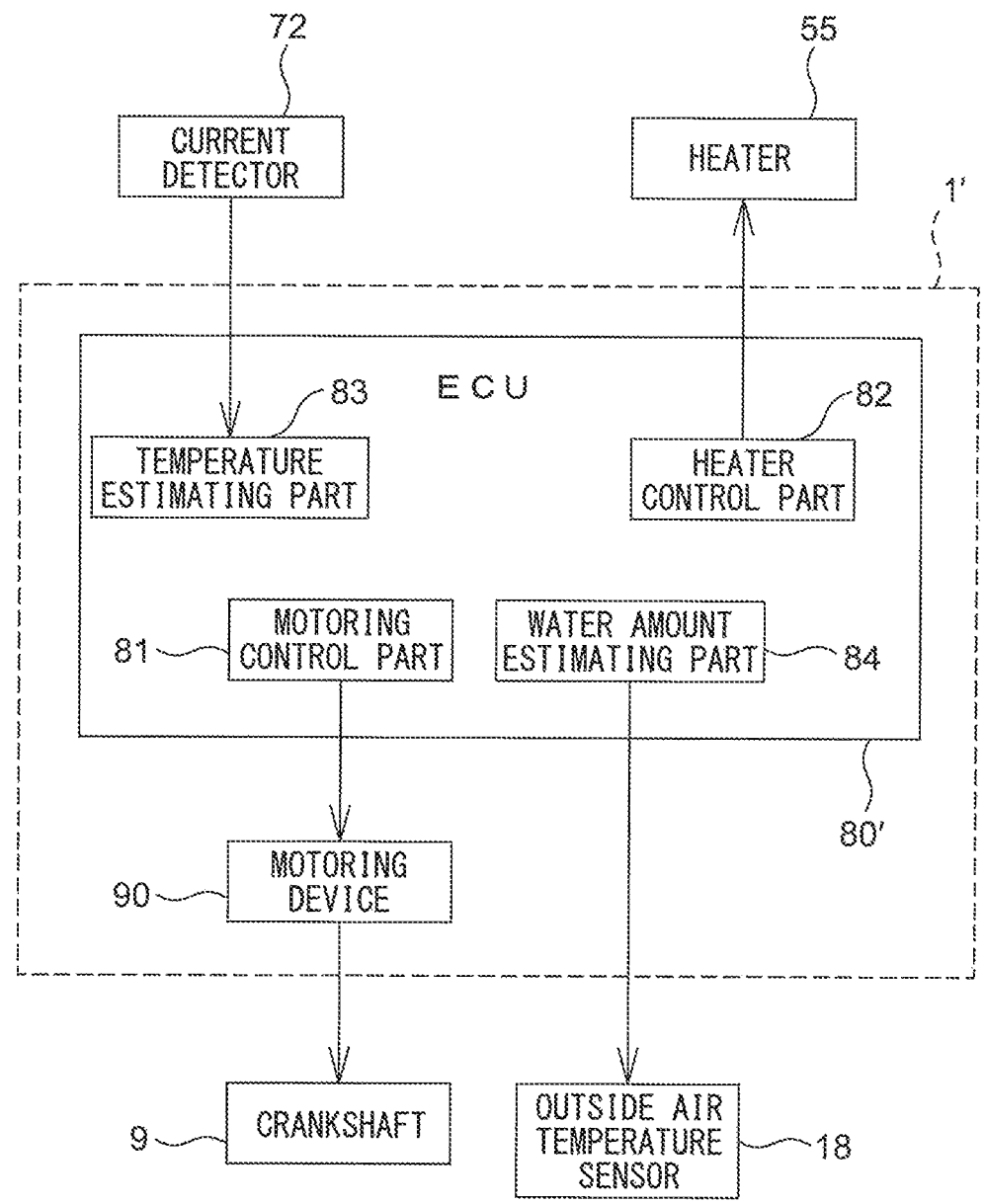
FIG. 8 is a block diagram schematically showing the configuration of a control system of an internal combustion engine etc., according to a second embodiment of the present disclosure.

FIG. 8 is a block diagram schematically showing the configuration of a control system of an internal combustion engine 1' etc., according to the second embodiment of the present disclosure. The control system of an internal combustion engine 1' is provided with a motoring device 90 and an electronic control unit (ECU) 80'. The ECU 80' includes a motoring control part 81, heater control part 82, temperature estimating part 83, and water amount estimating part 84. Therefore, the control system of an internal combustion engine 1' is provided with the motoring control part 81, heater control part 82, temperature estimating part 83 and water amount estimating part 84.

The water amount estimating part 84 estimates an amount of water present inside the sensor cover 11 of the air-fuel ratio sensor 10 (below, referred to as the "water amount WA"). Specifically, the water amount estimating part 84 estimates the temperature of the sensor cover 11 and estimates the water amount WA based on the estimated temperature of the sensor cover 11. The water amount WA is for example calculated by the following formula:

$$WA = \Sigma(WA_t) + WA_0$$

In the above formula, $WA_t$ is the amount of water produced per unit time inside the sensor cover 11, while $\Sigma(WA_t)$ is the value obtained by cumulatively adding the $WA_t$ during the operating time of the internal combustion engine 31. When the estimated temperature of the sensor cover 11 is the dew point (53° C.) or less, the water vapor in the exhaust gas condenses and condensed water is produced inside the sensor cover 11. For this reason, $WA_t$ is made a positive value when the estimated temperature of the sensor cover 11 is the dew point or less. Further, when the estimated temperature of the sensor cover 11 is a temperature between the dew point and the boiling point of water, the amount of water inside the sensor cover 11 does not change much at all. For this reason, $WA_t$ is made zero when the estimated temperature of the sensor cover 11 is a temperature between the dew point and the boiling point of water. Further, when the estimated temperature of the sensor cover 11 is the boiling point of water or more, the water inside the sensor cover 11 evaporates. For this reason, $WA_t$ is made a negative value when the estimated temperature of the sensor cover 11 is the boiling point of water or more. Further, $WA_0$ is the amount of water remaining inside the sensor cover 11 when the internal combustion engine 31 was stopped the previous time.

Figure 9:
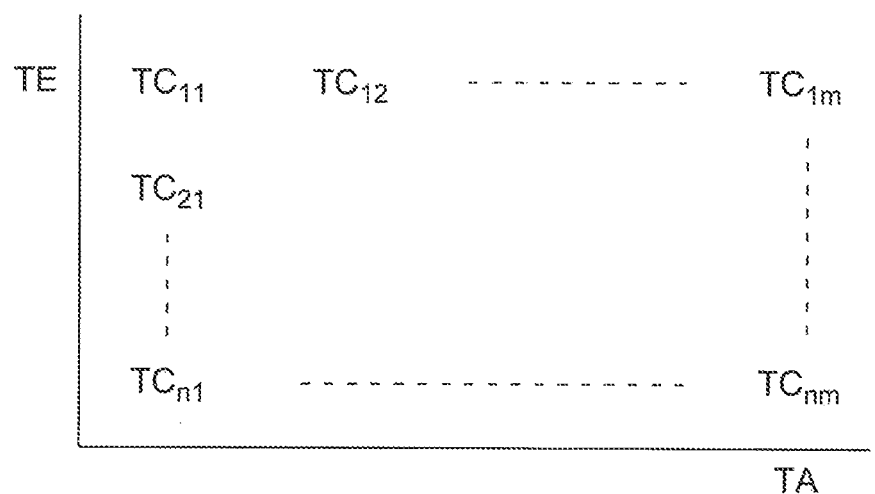
FIG. 9 is a graph showing a relationship between a temperature of a sensor element and outside air temperature of an internal combustion engine, and a temperature of a sensor cover.

Further, the water amount estimating part 84, for example, uses a map to estimate the temperature of the sensor cover 11 based on the temperature of the sensor element 12 and the outside air temperature of the internal combustion engine 31. The temperature of the sensor element 12, like in the first embodiment, is estimated by the temperature estimating part 83. The outside air temperature of the internal combustion engine is detected by the outside air temperature sensor 18 provided at the vehicle 30. In the map, as shown by FIG. 9, the temperature TC of the sensor cover 11 is shown as a function of the temperature TE of the sensor element 12 and outside air temperature TA of the internal combustion engine 31. Note that, the water amount estimating part 84 may use a map showing the relationship between the temperature of the sensor element 12 and the temperature of the sensor cover 11 to estimate the temperature of the sensor cover 11 based on the temperature of the sensor element 12. In this case, the outside air temperature sensor 18 may be omitted.

The motoring control part 81 controls the drive operation of the motoring device 90 based on the water amount WA estimated by the water amount estimating part 84. Specifically, the motoring control part 81 stops driving the motoring device 90 when the water amount WA estimated by the water amount estimating part 84 is a predetermined reference value or less even when the temperature of the sensor element 12 estimated by the temperature estimating part 83 is outside the cracked element temperature region. Further, the motoring control part 81 lengthens the drive time of the motoring device 90 when the water amount WA estimated by the water amount estimating part 84 is relatively large compared to when the water amount WA is relatively small. Due to the above-mentioned control, when the water amount WA is small, the drive time of the motoring device 90 can be made zero or can be shortened, so it is possible to reduce the electric power consumed by the motoring device 90.

<Control Routine of Processing for Estimating Water Amount>

Figure 10:
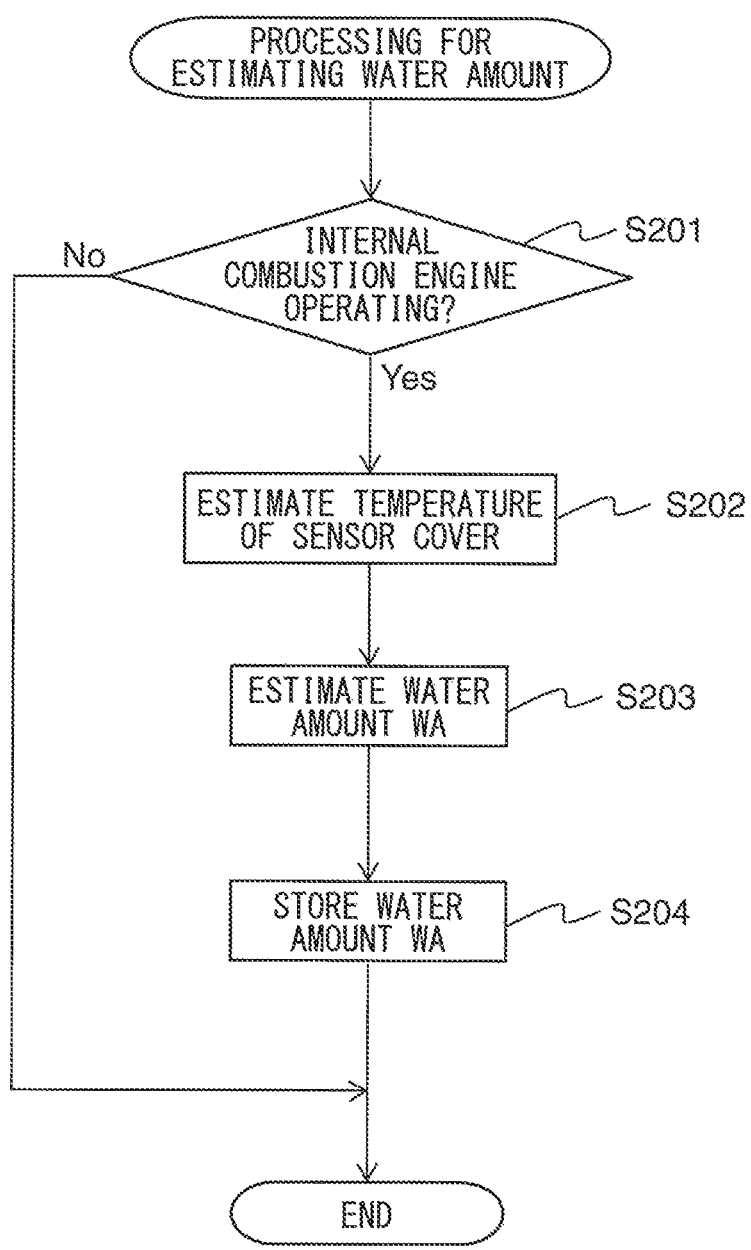
FIG. 10 is a flow chart showing a control routine of processing for estimating an amount of water in the second embodiment of the present disclosure.

FIG. 10 is a flow chart showing a control routine of processing for estimating the water amount in the second embodiment of the present disclosure. The present control routine is repeatedly executed by the ECU 80' while the ignition switch of the vehicle 30 is on. In the present control routine, the value of the water amount WA is updated during operation of the internal combustion engine 31.

First, at step S201, the water amount estimating part 84 judges whether the internal combustion engine 31 is operating. Note that, "the internal combustion engine 31 is operating" means the state where an air-fuel mixture is being burned in the cylinders 3. If at step S201 it is judged that the internal combustion engine 31 is not operating, the present control routine is ended. On the other hand, if at step S201 it is judged that the internal combustion engine 31 is operating, the present control routine proceeds to step S202.

At step S202, the water amount estimating part 84 estimates the temperature of the sensor cover 11 by any of the above methods. Next, at step S203, the water amount estimating part 84 estimates the water amount WA by the above-mentioned method based on the temperature of the sensor cover 11 estimated at step S202. Next, at step S204, the water amount estimating part 84 stores the water amount WA estimated at step S203 in the RAM of the ECU 80'. After step S204, the present control routine ends.

<Control Routine of Processing for Draining Water>

Figure 11:
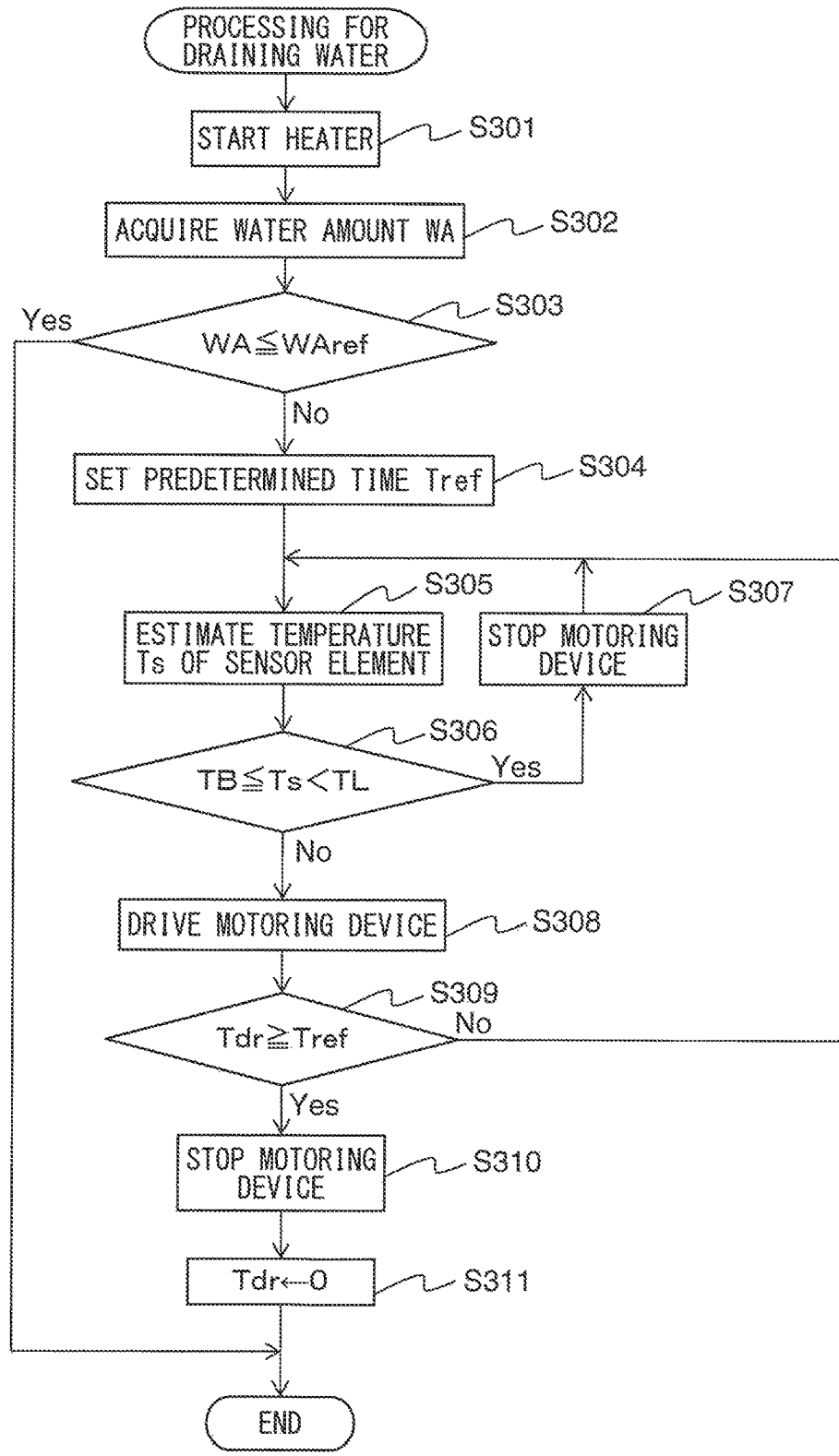
FIG. 11 is a flow chart showing a control routine of processing for draining water in the second embodiment of the present disclosure.

FIG. 11 is a flow chart showing a control routine of processing for draining water in the second embodiment of the present disclosure. The present control routine is executed by the ECU 80' when the ignition switch of the vehicle 30 is turned on. In the present control routine, the drive operation of the motoring device 90 is controlled so as to prevent a cracked element of the air-fuel ratio sensor 10 while draining water inside the sensor cover 11.

First, at step S301, in the same way as step S101 of FIG. 11, the heater control part 82 starts the heater 55. Next, at step S302, the motoring control part 81 acquires the water amount WA from the RAM of the ECU 80'.

Next, at step S303, the motoring control part 81 judges whether the water amount WA is a reference value WAref or less. The reference value WAref is the upper limit value of the water amount WA not obstructing the rise in temperature of the sensor element 12 at the time of heating by the heater 55 and is calculated in advance by experiments or calculation. The reference value WAref may be zero. If at step S303 it is judged that the water amount WA is the reference value WAref or less, the present control routine is ended without driving the motoring device 90. On the other hand, if at step S303 it is judged that the water amount WA is greater than the reference value WAref, the present control routine proceeds to step S304.

Figure 12:
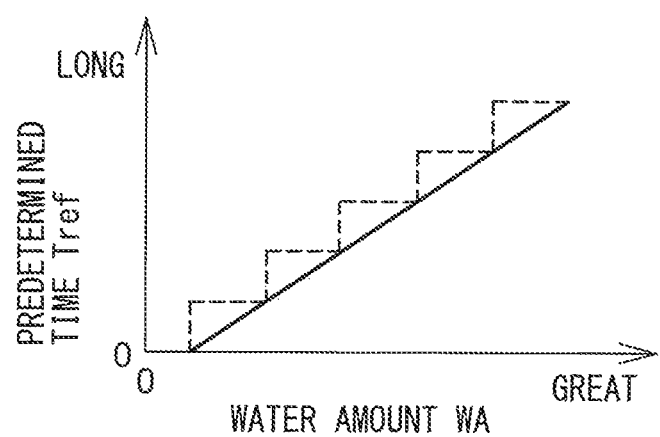
FIG. 12 is a map showing a relationship between an amount of water and a predetermined time.

At step S304, the motoring control part 81 sets a predetermined time Tref. The predetermined time Tref is a value used at the later step S309 and corresponds to the total drive time of the motoring device 90. Specifically, the motoring control part 81 lengthens the predetermined time Tref when the water amount WA is relatively large compared to when the water amount WA is relatively small. For example, the motoring control part 81 uses the map such as shown in FIG. 12 to set the predetermined time Tref. In this map, the predetermined time Tref is shown as a function of the water amount WA. As shown by the solid line in FIG. 12, the predetermined time Tref is made linearly longer as the water amount WA becomes greater. Note that, the predetermined time Tref, as shown by the broken line in FIG. 12, may be made longer in stages (in steps) as the water amount WA becomes greater.

After step S304, the present control routine proceeds to step S305. Step S305 to step S311 are similar to step S102 to step S108 of FIG. 7, so explanations will be omitted.

Other Embodiments

Above, embodiments were explained, but the present disclosure is not limited to these embodiments and can be modified and changed in various ways within the language of the claims. For example, the vehicle to which the control system of an internal combustion engine is applied may be a series type hybrid vehicle in which only the motor is used as a drive source of the wheel shaft, a plug-in hybrid vehicle whose battery can be charged by an outside power source, etc. Further, the vehicle to which the control system of an internal combustion engine is applied may be provided with only an internal combustion engine as a drive source of the wheel shaft so long as being provided with a motoring device.

Further, the sensor element of the exhaust sensor may be provided with another electrochemical cell in addition to a sensor cell. The other electrochemical cell may be, for example, a pump cell pumping out oxygen in a measured gas from a measured gas chamber, a monitor cell detecting a concentration of a specific component in the measured gas, etc. Further, the exhaust sensor may be an oxygen sensor detecting oxygen in the exhaust gas to thereby detect whether the air-fuel ratio of the exhaust gas is rich or lean. Further, the exhaust sensor may be a nitrogen oxide sensor ($NO_x$ sensor) detecting a concentration of nitrogen oxides ($NO_x$) in the exhaust gas, a sulfur oxide sensor ($SO_x$ sensor) detecting a concentration of sulfur oxides ($SO_x$) in the exhaust gas, etc.

The invention claimed is:

1. A control system of an internal combustion engine controlling an internal combustion engine comprising an exhaust sensor arranged in an exhaust passage and detecting a specific component in exhaust gas, wherein
   the exhaust sensor comprises a sensor element, a sensor cover covering the sensor element, and a heater heating the sensor element,
   the control system comprises
   a motoring device driving rotation of a crankshaft of the internal combustion engine,
   a motoring control part configured to control the motoring device,
   a heater control part configured to control supply of electric power to the heater, and
   a temperature estimating part configured to estimate a temperature of the sensor element, and
   the motoring control part configured to drive the motoring device for a predetermined time when the temperature of the sensor element estimated by the temperature estimating part is outside a predetermined cracked element temperature region while the heater control part is supplying electric power to the heater, and stop driving the motoring device when the temperature of the sensor element is within the cracked element temperature region.

2. The control system of an internal combustion engine according to claim 1, further comprising a water amount estimating part estimating an amount of water present inside the sensor cover, wherein the motoring control part is configured to control the motoring device based on the amount of water estimated by the water amount estimating part.

3. The control system of an internal combustion engine according to claim 2, wherein the motoring control part is configured to stop driving the motoring device when the amount of water estimated by the water amount estimating part is a predetermined reference value or less even when the temperature of the sensor element estimated by the temperature estimating part is outside the cracked element temperature region.

4. The control system of an internal combustion engine according to claim 2, wherein the motoring control part is configured to lengthen the predetermined time when the amount of water estimated by the water amount estimating part is relatively large compared to when the amount of water is relatively small.

5. The control system of an internal combustion engine according to claim 3, wherein the motoring control part is configured to lengthen the predetermined time when the amount of water estimated by the water amount estimating part is relatively large compared to when the amount of water is relatively small.

6. The control system of an internal combustion engine according to claim 1, wherein the temperature estimating part is configured to estimate the temperature of the sensor element based on the total of the electric power supplied to the heater.

7. The control system of an internal combustion engine according to claim 2, wherein the temperature estimating part is configured to estimate the temperature of the sensor element based on the total of the electric power supplied to the heater.

8. The control system of an internal combustion engine according to claim 3, wherein the temperature estimating part is configured to estimate the temperature of the sensor element based on the total of the electric power supplied to the heater.

9. The control system of an internal combustion engine according to claim 4, wherein the temperature estimating part is configured to estimate the temperature of the sensor element based on the total of the electric power supplied to the heater.

10. The control system of an internal combustion engine according to claim 5, wherein the temperature estimating part is configured to estimate the temperature of the sensor element based on the total of the electric power supplied to the heater.

\* \* \* \* \*